(12) United States Patent
Kimmlingen et al.

(10) Patent No.: US 10,036,794 B2
(45) Date of Patent: Jul. 31, 2018

(54) PATIENT COUCH WITH FLEXIBLE RF TRANSMITTING POWER DISTRIBUTION FOR A MAGNETIC RESONANCE TOMOGRAPHY SYSTEM

(71) Applicants: Ralph Kimmlingen, Zirndorf (DE); Norbert Rietsch, Dormitz (DE)

(72) Inventors: Ralph Kimmlingen, Zirndorf (DE); Norbert Rietsch, Dormitz (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/639,410

(22) Filed: Jun. 30, 2017

(65) Prior Publication Data

US 2018/0003791 A1 Jan. 4, 2018

(30) Foreign Application Priority Data

Jul. 1, 2016 (DE) ........................ 10 2016 212 043

(51) Int. Cl.
| | |
|---|---|
| *A61B 5/055* | (2006.01) |
| *G01R 33/563* | (2006.01) |
| *A61B 6/04* | (2006.01) |
| *G01R 33/54* | (2006.01) |
| *G01R 33/561* | (2006.01) |

(52) U.S. Cl.
CPC ...... *G01R 33/56383* (2013.01); *A61B 5/0555* (2013.01); *A61B 6/0442* (2013.01); *G01R 33/543* (2013.01); *G01R 33/561* (2013.01); *G01R 33/563* (2013.01)

(58) Field of Classification Search
CPC .. A61B 5/0555; A61B 6/0442; G01R 33/543; G01R 33/561; G01R 33/563; G01R 33/56383
See application file for complete search history.

(56) References Cited

U.S. PATENT DOCUMENTS

| | | | |
|---|---|---|---|
| 2003/0088175 A1 | 5/2003 | Branch et al. | |
| 2011/0221441 A1* | 9/2011 | Baumgartl | G01R 33/3415 324/322 |
| 2014/0088403 A1 | 3/2014 | Gross | |
| 2016/0178712 A1* | 6/2016 | Biber | G01R 33/34046 600/422 |

FOREIGN PATENT DOCUMENTS

| | | |
|---|---|---|
| CN | 203576502 U | 5/2014 |
| DE | 102012217439 A1 | 2/2014 |
| WO | WO2008122117 A1 | 10/2008 |

OTHER PUBLICATIONS

German Office Action for German Application No. 10 2016 212 043.3 dated Mar. 23, 2017, with English Translation.

* cited by examiner

*Primary Examiner* — Ruth S Smith

(74) *Attorney, Agent, or Firm* — Lempia Summerfield Katz LLC

(57) ABSTRACT

A patient couch for a magnetic resonance tomography system and a magnetic resonance tomography system are provided. The patient couch includes a feed facility for radiofrequency energy having a plurality of conduction paths for feeding radiofrequency energy. The patient couch also includes a plurality of plug-in connectors for local coils having a transmit coil, and a distribution structure for the distribution of radiofrequency energy from the feed facility to the plug-in connectors.

14 Claims, 4 Drawing Sheets

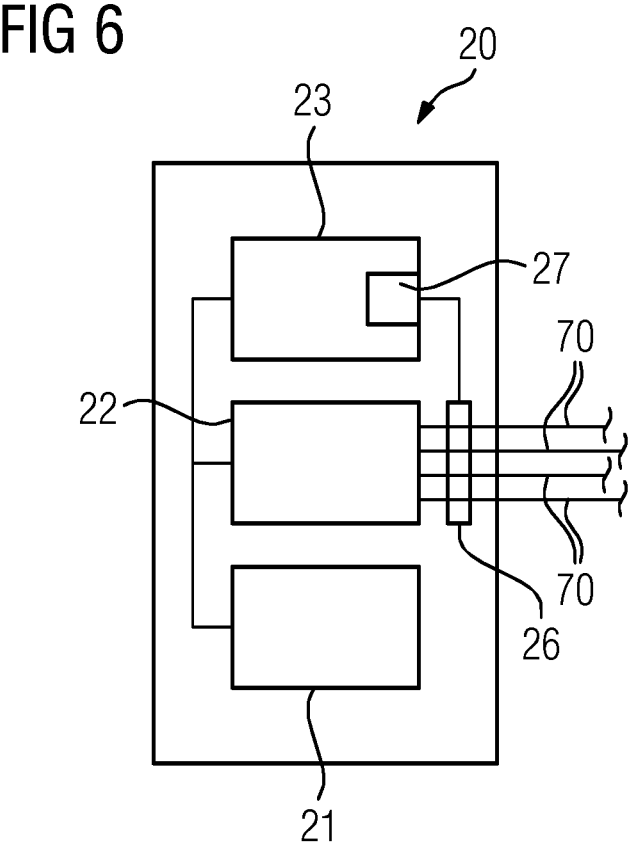

a plurality of conduction paths for feeding radiofrequency energy. All the electrical connections that are capable of transmitting radiofrequency energy are regarded as a conduction path in the context of the present embodiments. The feed facility may, for example, provide cables fixedly connected to the patient couch (e.g., coaxial cables), where the cables have individual or common plug-in connectors at the opposite end thereof to the patient couch. The feed facility may, however, equally include a plurality of radiofrequency plug-in connections on the patient couch, via which cables for feeding radiofrequency energy may be connected. The feed facility in question may, however, also be one or more multipole plug-in connections, by which a plurality of individual cables or cable bundles may be plugged in.

PATIENT COUCH WITH FLEXIBLE RF TRANSMITTING POWER DISTRIBUTION FOR A MAGNETIC RESONANCE TOMOGRAPHY SYSTEM

This application claims the benefit of DE 10 2016 212 043.3, filed on Jul. 1, 2016, which is hereby incorporated by reference in its entirety.

BACKGROUND

The present embodiments relate to a patient couch for a magnetic resonance tomography system having a plug-in connector for a local coil.

Magnetic resonance tomography systems are imaging devices that, in order to image an object under examination, align nuclear spins of the object under examination with a strong external magnetic field and excite the nuclear spins by an alternating magnetic field to precess about the alignment. The precession or return of the spins from the excited state to a state with a lower energy in turn generates an alternating magnetic field as a response (e.g., a magnetic resonance signal) that is received via antennas.

With the aid of magnetic gradient fields, a position encoding that subsequently enables an association of the received signal with a volume element is imparted to the signals. The received signal is then evaluated, and a three-dimensional imaging display of the object under examination is provided.

In order to excite the precession of the spins, alternating magnetic fields having a frequency that corresponds to the Larmor frequency at the respective static magnetic field strength and having very high field strengths or power levels are to be provided. In order to improve the signal-to-noise ratio of the magnetic resonance signal received by the antennas, antennas frequently referred to as local coils that are arranged directly on the patient are used.

In the case of high magnetic fields (e.g., at 3 T and greater), Larmor frequencies of greater than 100 MHz result. At these frequencies, the absorption in the human body increases significantly at the same time interference effects results at the wavelengths of 2 m and less within the area occupied by the patient in the patient tunnel. This provides that a homogeneous field strength of the exciting alternating magnetic field B1 and thus a homogeneous excitation with a single body coil surrounding the body is no longer ensured.

In order to avoid image artifacts caused thereby, local coils with transmit coils that are arranged individually or as an array on the body in the immediate vicinity of a region under examination are also used. The transmit coils, however, are not to be supplied with radiofrequency energy of the excitation signal to be sent, which attains power levels of several hundred watts up to kilowatts. A low-loss transmission of the power level provides that correspondingly thick coaxial cables that are then also correspondingly rigid and difficult to handle are used.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a patient couch and a magnetic resonance tomography system that are easier to handle and cheaper are provided.

The patient couch for a magnetic resonance tomography system, according to one or more of the present embodiments, has a feed facility for radiofrequency energy having a plurality of conduction paths for feeding radiofrequency energy. All the electrical connections that are capable of transmitting radiofrequency energy are regarded as a conduction path in the context of the present embodiments. The feed facility may, for example, provide cables fixedly connected to the patient couch (e.g., coaxial cables), where the cables have individual or common plug-in connectors at the opposite end thereof to the patient couch. The feed facility may, however, equally include a plurality of radiofrequency plug-in connections on the patient couch, via which cables for feeding radiofrequency energy may be connected. The feed facility in question may, however, also be one or more multipole plug-in connections, by which a plurality of individual cables or cable bundles may be plugged in.

The patient couch according to one or more of the present embodiments has a plurality of plug-in connectors for local coils. In this situation, these may, for example, be single-pole or multipole connectors or sockets for radiofrequency transmission.

The patient couch has a distribution structure for the distribution of radiofrequency energy from the feed facility to the plug-in connectors. In this situation, the distribution structure may simply include electrical radiofrequency connections such as coaxial cables, striplines, or similar, but may also include circuits for adjustment of the lines or power couplers for the merging or distribution of fed radiofrequency power. The circuits, for example, may have inductances and/or capacitances or also switching elements for the controllable distribution of radiofrequency energy.

The magnetic resonance tomography system according to one or more of the present embodiments has a patient couch. The magnetic resonance tomography system has a plurality of transmitting power outputs. In the context of the present embodiments, all the electrical connections that are capable of delivering radiofrequency energy for excitation of the nuclear spins (e.g., power amplifiers or distribution networks fed by power amplifiers) are regarded as transmitting power outputs. Each transmitting power output of the plurality of transmitting power outputs has a plurality of electrical connections to the feed facility for the transmission of radiofrequency energy. The feed facility for the patient couch may therefore be connected to the transmitting power outputs of the magnetic resonance tomography system such that radiofrequency energy may be fed via the plurality of conduction paths to the patient couch.

In an advantageous manner, the patient couch according to one or more of the present embodiments and the magnetic resonance tomography system according to one or more of the present embodiments enable a distributed feed of the radiofrequency energy via a plurality conduction paths. The individual conduction paths may thus transmit a lower power level and may therefore be thinner, more flexible, and easier to handle.

In one embodiment of the patient couch, the distribution structure connects at least two conduction paths of the feed facility electrically to a plug-in connector for local coils having a transmit coil.

In an advantageous manner, the distribution structure allows plug-in connectors on the patient couch and thereby local coils that may be connected thereto to be supplied via a plurality of conduction paths. The plurality of conduction paths may thus also to be supplied with higher power levels than an individual conduction path would be capable of transmitting. In one embodiment, a plurality of antenna coils are supplied with radiofrequency energy simultaneously in the local coil.

In one embodiment of the patient couch, the distribution structure has a power coupler configured to combine the signals of the at least two conduction paths to form a single conduction path. In one embodiment, the distribution structure has a combination network configured to merge the radiofrequency energy of two conduction paths to form a single signal line on the plug-in connector.

In one embodiment, the patient couch makes it possible for the local coil to have a power coupler or combination network. The power coupler merges the radiofrequency energy of two conduction paths in order to supply one antenna coil and thus also adequately supplies local coils having a higher power requirement for a transmit coil on a single terminal of the plug-in connector with radiofrequency energy.

In one embodiment of the patient couch, the distribution structure has a plurality of flexible lines. These may, for example, be coaxial conductors, symmetrical lines, striplines, or similar lines suitable for the conduction of radiofrequency alternating currents. By preference, the flexible lines are embodied completely or at least in part on flexible printed circuit boards. In this situation, for example, signals having the Larmor frequency of a magnetic resonance tomography system, for which the patient couch is intended, are considered to be radiofrequency. Frequencies higher than 50 MHz, 100 MHz, or 150 MHz, for example, are consequently to be regarded as radiofrequency.

In one embodiment of the patient couch, at least one of the plug-in connectors is arranged in movable fashion on the patient couch. In this situation, the plug-in connector is movable in two dimensions (e.g., at least in one direction along a longitudinal extension of the patient couch).

A movable plug-in connector permits a flexible positioning of the local coil on a patient without providing, on the local coils, lines that are long, unwieldy, and thereby also electrically critical on account of possible sheath currents.

In one embodiment of the patient couch, the patient couch has a position generator for determining a relative position of the plug-in connector with respect to the patient couch. In this situation, the patient couch is embodied such that the position information from the position generator may be captured by a controller of the magnetic resonance tomography system.

The position generator may be used to ascertain the position of the plug-in connector in relation to the patient couch and thus also in relation to a field magnet of a magnetic resonance tomography system. If the connection of the local coil to the plug-in connector is, for example, rigid, then the position of the local coil is also known, and the controller of the magnetic resonance tomography system may, depending on the position, control the power level or modify the transmitter pulses.

In one embodiment of the patient couch, the patient couch has a second feed facility for radiofrequency energy having a plurality of parallel conduction paths and a second distribution structure for the distribution of radiofrequency energy from the second feed facility to the plug-in connectors.

A second feed facility on the patient couch, such that, for example, the first feed facility is provided at the head end of the patient couch and the second feed facility at the foot end, permits smaller distances between the plug-in connectors and the feed facility. This provides that the length of the connections in the distribution structures may be reduced in an advantageous manner. For example, plug-in connectors for a knee coil may be connected to the feed facility at the foot end while plug-in connectors for a head coil or chest coil are connected to the feed facility at the head end.

In one embodiment of the magnetic resonance tomography system, the magnetic resonance tomography system has a local coil having a transmit coil. A power coupler is provided in a housing of the local coil in this situation.

If the power coupler is only provided in the local coil, the connection structure between the patient couch and the local coil may be embodied using thin and flexible lines because a higher power level occurs only in the local coil as a result of the combination of two connection lines.

In one embodiment of the magnetic resonance tomography system, the magnetic resonance tomography system has a local coil having a transmit coil and a housing that is arranged in a predetermined position relative to a local coil connector. In this situation, the housing may be connected rigidly or elastically to the local coil connector such that when the local coil connector is plugged into the plug-in connector, the position of the local coil relative to the plug-in connector is also predetermined. Elastically is regarded as the case in which although the connection between local coil connector and local coil is deformed slightly under the influence of a force, thereafter the connection does however return again to a predetermined form (e.g., also under the influence of weight of the local coil).

Using the predetermined position of the local coil in relation to the local coil connector in the plugged-in state, the position of the local coil relative to the patient couch and the magnetic resonance tomography system may be determined.

In an embodiment of the magnetic resonance tomography system having a patient couch with movable plug-in connectors and a position generator, a controller of the magnetic resonance tomography system is configured to control a transmitter pulse via the transmit coil of the local coil depending on the position of the plug-in connector relative to the patient couch. The position generator captures the position of the plug-in connector.

The controller of the magnetic resonance tomography system according to one or more of the present embodiments may determine the position of the local coil relative to the patient couch via the position generator and may, given the known position of the patient couch, determine the position relative to the field magnet. Using this information, the controller may adapt the transmit power and/or the pulse shape and/or frequency to the position of the local coil and thus, for example, reduce the SAR exposure.

In one embodiment of the magnetic resonance tomography system, the plurality of electrical connections on the feed facility are embodied in releasable fashion.

In one embodiment, the releasable connection makes it possible to separate the patient couch from the magnetic resonance tomography system, for example, in order to prepare a patient.

In one embodiment of the magnetic resonance tomography system, the patient couch is arranged in a patient tunnel of a field magnet of the magnetic resonance tomography system during an imaging measurement. In this situation, the distribution structure is arranged in the vicinity of a conducting surface such that a reaction from an alternating electromagnetic field, which is emitted by a transmit coil connected to a plug-in connector, is reduced. For example, the distribution structure may be routed close to a shielding structure between the patient tunnel and the superconducting magnet. Close in this situation is considered to be a distance that is less than one tenth, one twentieth, one fiftieth, or one hundredth of a wavelength of an electromagnetic wave having the Larmor frequency. In one embodiment, the distribution structure is in mechanical contact with the conducting surface over a longer section (e.g., over more than half the extent of the distribution structure). By preference, the conducting surface is connected electrically at one point to a ground of the MRT.

At the surface of a metallic shield, all the electrical field components parallel to the surface are equal to zero. On account of the continuity of the fields, the same essentially also applies to the electrical fields in the vicinity of the surface, where vicinity expresses the fact that the distance is small compared with the wavelength of an associated alternating electromagnetic field. Small in this context may, for example, be smaller by a factor of 10, 20, 50 or 100. For an electrical conductor that is routed close to the surface, almost no electrical potential therefore builds up along the extent along the surface as a result of the alternating electromagnetic field. With regard to an arrangement of the distribution structure according to one or more of the present embodiments, the formation of sheath currents is therefore reduced, and sheath current traps for conductors of the distribution structure may be smaller and/or simpler or may even be dispensed with entirely. Effects of disturbances that are given off via the distribution structure and impact on the local coil (e.g., in the case of receiving) are also reduced.

In an embodiment of the magnetic resonance tomography system, the magnetic resonance tomography system has a plurality of power sensors and a monitoring unit. The power sensors are configured to monitor a radiofrequency energy flow through the plurality of electrical connections between the transmitting power outputs and the feed facility. By preference, a radiofrequency power level flowing in the direction of the patient couch through the individual electrical connections is captured. This may, for example, be a direct capture by directional couplers, or also an indirect capture by capturing one radiofrequency power level flowing back and one radiofrequency power level generated in an assigned power amplifier. The monitoring unit is configured to monitor the observance of SAR limit values using values captured by the power sensors (e.g., by comparing the captured measurement values with predetermined threshold values or firstly summing and then comparing). If one or more threshold values is/are exceeded, the transmitting power output(s) concerned may then be interrupted or a corresponding power level may be reduced.

In one embodiment, the monitoring of the radiofrequency power level may take place via the electrical connections using power sensors that are more cost-effective because the power levels to be captured are distributed over a plurality of electrical connections and are thereby considerably lower.

BRIEF DESCRIPTION OF THE DRAWINGS

FIG. 6 shows a schematic diagram of an embodiment of a control unit of a magnetic resonance tomography system.

DETAILED DESCRIPTION

Figure 1:
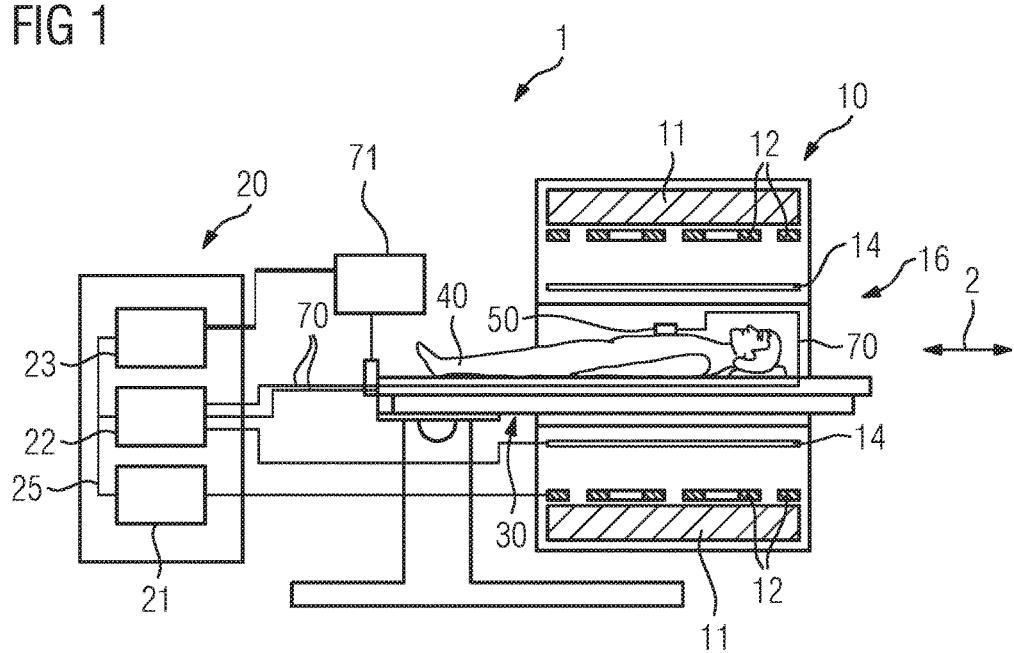
FIG. 1 shows a schematic diagram of an embodiment of a magnetic resonance tomography system.

FIG. 1 shows a schematic diagram of an embodiment of a magnetic resonance tomography system 1 including a patient couch 30.

The magnet unit 10 has a field magnet 11 that generates a static magnetic field B0 to align nuclear spins of samples or in a body of a patient 40 in an acquisition area. The acquisition area is arranged in a patient tunnel 16 that extends in a longitudinal direction 2 through the magnet unit 10. The field magnet 11 in question may be a superconducting magnet that may provide magnetic fields having a magnetic flux density of up to 3 T, or even higher, in the latest devices. For lower field strengths, however, permanent magnets or electromagnets with normal-conducting coils may also be used.

The magnet unit 10 has gradient coils 12 that are configured to overlay the magnetic field B0 with variable magnetic fields in three spatial directions for the spatial differentiation of the captured imaging regions in the sample volume. The gradient coils 12 are normally coils made of normal-conducting wires that may generate fields orthogonal to one another in the sample volume.

The magnet unit 10 also has a body coil 14 that is configured to give off a radiofrequency signal fed via a signal line into the sample volume, and to receive resonance signals emitted by the patient 40 and deliver the resonance signals via a signal line. The magnetic resonance tomography system according to one or more of the present embodiments has one or more local coils 50 that are arranged in the patient tunnel 16 close to the patient 40.

A control unit 20 supplies the magnet unit 10 with the various signals for the gradient coils 12 and the body coil 14 and evaluates the signals received.

Thus, the control unit 20 has a gradient control 21 configured to provide the gradient coils 12 with variable currents via feed lines. The variable currents provide the desired gradient fields in the sample volume on a temporally coordinated basis.

The control unit 20 has a radiofrequency unit 22 that is configured to generate a radiofrequency pulse with a predetermined time characteristic, amplitude, and spectral power distribution to excite a magnetic resonance of the nuclear spins in the patient 40. In this case, pulse powers in the kilowatt range may be achieved. The individual units are connected to one another via a signal bus 25.

The radiofrequency signal generated by the radiofrequency unit 22 is provided at a plurality of transmitting power outputs and fed to the patient couch 30 via a plurality of conduction paths 70 and distributed via a distribution structure 60 not visible in FIG. 1 to one or more local coils 50 and emitted into the body of the patient in order to excite the nuclear spins there.

The local coil 50 may then receive a magnetic resonance signal from the body of the patient 40; this is because the signal-to-noise ratio (SNR) of the local coil 50 is better on account of the small distance than in the case of being received by the body coil 14. The MR signal received by the local coil 50 is processed in the local coil 50 and forwarded to the radiofrequency unit 22 of the magnetic resonance tomography system 1 for evaluation and image acquisition. By preference, the distribution structure 60 and the conduction paths 70 are again utilized for this purpose, but separate signal connections or wireless transmission may also be provided. In one embodiment, special local coils or other antennas are provided for receiving.

Figure 2:
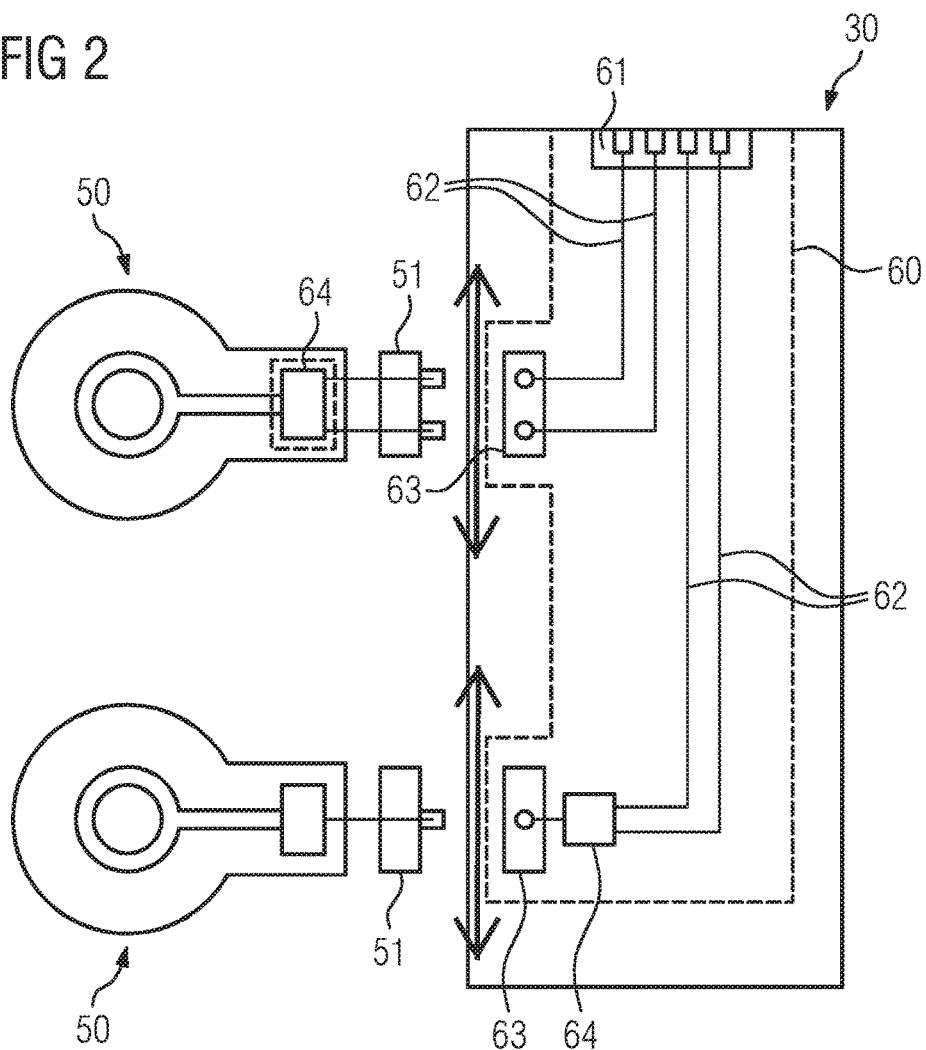
FIG. 2 shows a schematic diagram of an embodiment of a patient couch.

FIG. 2 shows a possible embodiment of a patient couch 30 in a schematic diagram.

For the sake of clarity, ground conductors or return conductors of signal connections are not illustrated separately in FIG. 2. In this situation, the individual lines that stand for signal connections represent both cores required for an electrical connection, whether it be the inner conductor and the shield of a coaxial cable, the two cores of a symmetrical line, or the signal conductor and the ground plane of a stripline.

The patient couch has a distribution structure 60 for high frequency, the elements whereof are grouped together logically in FIG. 2 by the dashed line. In the embodiment illustrated, the distribution structure 60 has a feed socket 61, via which the conduction paths 70 may be connected to the patient couch 30. In one embodiment, the conduction paths 70 are connected without a socket 61 (e.g., connected directly in non-releasable fashion to the distribution structure 60).

The distribution structure 60 has signal lines 62 that connect the feed socket 61 electrically to plug-in connectors 63 for local coils for transmitting radiofrequency energy. The signal lines 62 may, for example, as already mentioned, be coaxial lines, symmetrical lines, or striplines on a flexible circuit board. In one embodiment, the distribution structure 60 consists entirely or for the most part of a flexible or rigid printed circuit board.

In one embodiment, the plug-in connectors 63 may, in one embodiment, be arranged in a fixed position on the patient couch 30. In one embodiment, one or more of the plug-in connectors 63 are arranged in movable fashion in the patient couch 30 such that the plug-in connectors 63 are movable, for example, in the plane of the patient couch 30 illustrated in FIG. 2 in the direction of a longitudinal extension of the patient couch 30 and/or also transversely thereto. This may be implemented, for example, by routing the plug-in connectors 63 in cross-bars or grooves in the patient couch 30 and a flexible distribution structure 60 including, for example, thin coaxial cables or a flex board.

In one embodiment, the patient couch 30 includes one or more position generators 71 configured to capture the relative position of one or more movable plug in connectors 63 in relation to the patient couch 30. The position generators 71 may, for example, be configured to scan optical markers on the patient couch 30 or the plug in connector 63 and thus to capture a relative position. Mechanical coding that is captured by switches or light barriers, or an electrical capture of a variable resistance, capacitance, or inductance and also other electronic devices in order to capture a distance or a relative position may be provided. The position generator 71 is configured to transmit captured information via a signal connection to the controller 23 of the magnetic resonance tomography system 1. The signal connection is, for example, an electrical cable, a fiber optic cable, or a wireless connection. If the local coil 50 has a fixed connection to the local coil connector 51 (e.g., by the local coil connector 51 being arranged in the housing of the local coil 50), the position of the local coil 50 on the patient couch 30 is thereby also known to the controller 23.

In one embodiment, the controller 23 may be configured to optimize transmitter pulses emitted via the local coil 50 by using the information relating to the position of the local coil 50 and the information relating to the position of the patient couch 30 and thereby depending on the relative position of the plug-in connector 63 (e.g., by increasing the power level when the local coil 50 is located above non-sensitive body parts such as extremities).

In this situation, the feed socket 61 and/or the local coil sockets 63 may have any desired releasable connection systems for radiofrequency signals (e.g., coaxial connectors, surface contacts, spring contacts and/or also pin contacts, but also contactless connections such as a capacitive or inductive coupling).

The connection system 60 may also include power couplers 64 that make it possible to combine the signals and thereby also the power level from one or more signal lines 62 at one output. In this manner, the radiofrequency energy may be distributed on the conduction paths 70 onto a plurality of conduction paths 70, and therefore, thinner and more flexible lines may be used. As required, the plurality of conduction paths 70 may be merged by combination, and a high power level may be fed to a single local coil 50. In one embodiment, the power coupler 64 is provided not in the patient couch 30 itself but in the local coil 50. In one embodiment, the power coupler 64 is provided in a local coil connector 51, by which the local coil 50 may be connected to the patient couch 30.

Figure 3:
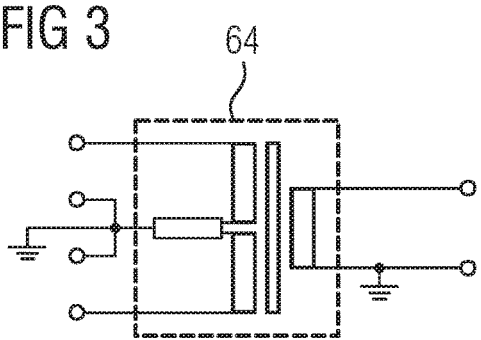
FIG. 3 shows a schematic of one embodiment of a power coupler for a patient couch.
Figure 4:
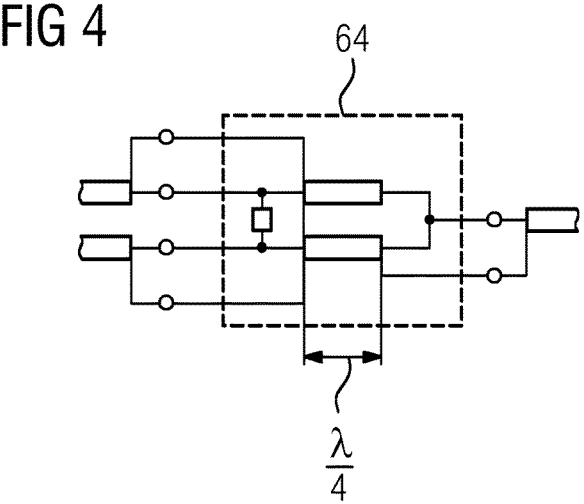
FIG. 4 shows a schematic of one embodiment of a power coupler for a patient couch.

FIG. 3 and FIG. 4 show possible exemplary embodiments of a power coupler.

The embodiment shown in FIG. 3 utilizes an inductive coupling or a transformer in order to merge the signals of two signal lines. The power coupler shown in FIG. 3 is not restricted to a single frequency. If, however, a ferrite core is used in order to increase the inductance, then the use in a magnetic resonance tomography system 1 may be rendered more difficult.

FIG. 4 shows a possible embodiment that is also non-critical in a strong magnetic field. In this situation, the waveguides having a length that corresponds to a quarter of the effective wavelength on the waveguide of the signal to be transmitted act as transformers, which are, however, frequency dependent.

In addition to the variants shown in FIGS. 3 and 4, a multiplicity of more complex networks consisting of resistances, inductances, and capacitances that permit a low-loss combination of two or more signals for one or more frequencies may also be provided as power couplers 64 in a patient couch 30 according to one or more of the present embodiments.

Figure 5:
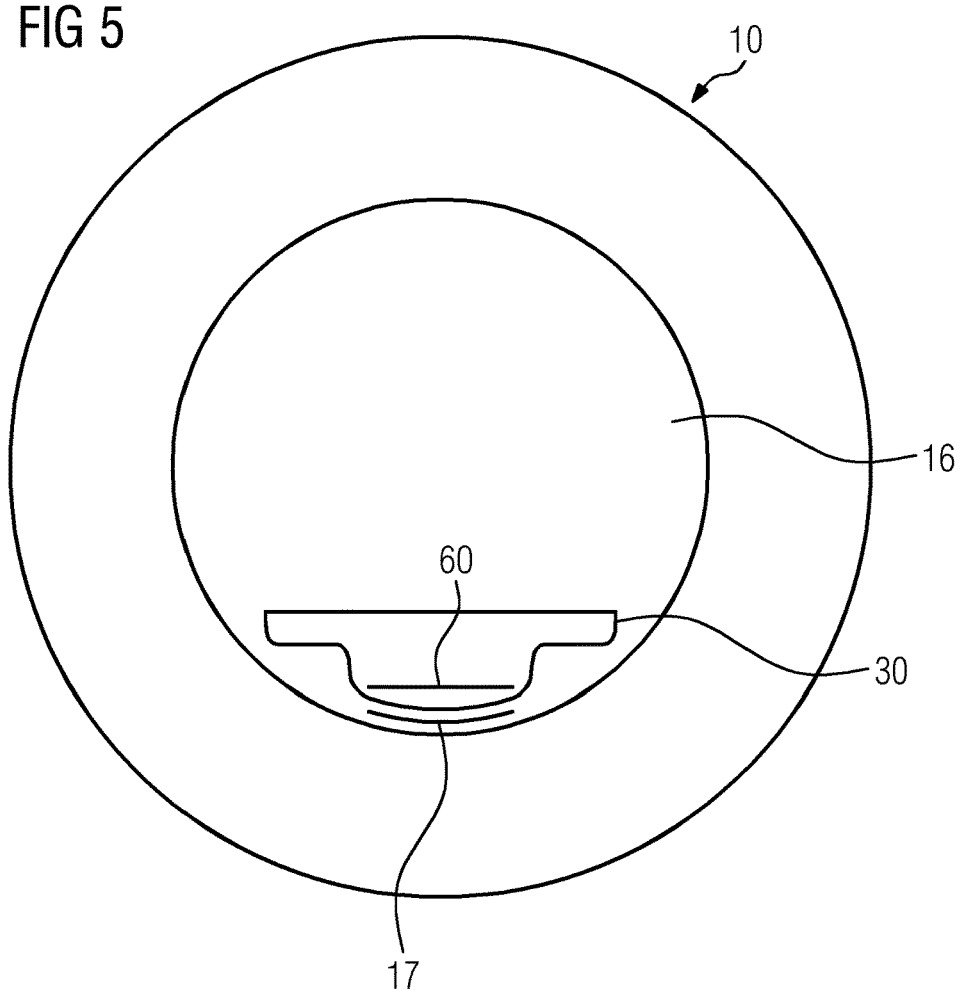
FIG. 5 shows a cross-section through a patient tunnel with an embodiment of a patient couch.

FIG. 5 shows a cross-section through a magnet unit 10, in the patient tunnel 16 whereof an embodiment of the patient couch 30 is arranged.

In this situation, the patient tunnel 16 has a conducting surface 17 that is arranged directly beneath the patient couch 30. Such types of conducting surfaces 17 may also be arranged between a wall of the patient tunnel 16 and other components such as gradient coil 12 or field magnet 11. In one embodiment, the conducting surface 17 is arranged in the patient couch 30 in the immediate vicinity of the wall of the patient tunnel 16.

Conducting surfaces exhibit the characteristic that electrical fields in the immediate vicinity have no electrical components that are tangential to the conducting surface. Accordingly, no significant voltages parallel to the conducting surface 17 may be induced even in signal lines 62 routed in the vicinity by the radiofrequency field in the patient tunnel 16. With the distribution structure 60 therefore being arranged in the immediate vicinity of the conducting surface 17, measures for suppressing induced waves or sheath currents may either be dispensed with entirely or be implemented in considerably simpler and considerably more cost-effective fashion Immediate vicinity in this situation is considered to be a distance between distribution structure 60 and conducting surface 17 of less than 1 cm, 5 cm, or 10 cm. Alternatively, immediate vicinity may be expressed in relation to the wavelength is less than one hundredth, one fiftieth, or one twentieth of the wavelength of the transmitter pulses and/or of the received magnetic resonance signals. In this situation, the distribution structure 60 is arranged in the immediate vicinity of the conducting surface 17 over an entire extent (e.g., length, width, or area) as far as possible (e.g., over at least 50, 80 or 90 percent of the extent). In one embodiment, the distribution structure lies entirely or partially on the conducting surface (e.g., electrically insulated).

FIG. 6 shows a schematic diagram of a control unit 20 of an embodiment of a magnetic resonance tomography system 1. The same objects are identified by the same reference characters as in FIG. 1.

The control unit 20 shown in FIG. 6 has a power sensor 26 that in each case captures a transmit power level that is output at a plurality of transmitting power outputs of the radiofrequency unit 22 to the conduction paths 70, and forwards a signal containing information about the transmit power levels output to a monitoring unit 27.

The monitoring unit 27 may, as shown in FIG. 6, be provided as part of a controller 23, or, for example, also as part of the radiofrequency unit 22, or independently of both. The monitoring unit 27 is configured to capture and to process the transmit power levels, and to compare values thus ascertained with one or more predetermined limit values. If a limit value is exceeded, the monitoring unit may output an alarm or directly interrupt an output of transmit power to the transmitting power outputs.

It is, for example, possible to monitor whether the power level at individual transmitting power outputs does not exceed predetermined limit values or the sum of the transmit power levels of a plurality of or all transmitting power outputs. The interruption may, for example, then be effected by the controller 23 via the signal bus 25.

Although the invention has been illustrated and described in detail using exemplary embodiments, the invention is not restricted by the disclosed examples. Other variations may be derived therefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for use in a magnetic resonance tomography system, the apparatus comprising:
    a patient couch;
    a feed facility for radiofrequency energy, wherein the feed facility has a plurality of conduction paths for feeding radiofrequency energy;
    a plurality of plug-in connectors for local coils having a transmit coil, wherein at least one plug-in connector of the plurality of plug in connectors is arranged in a movable fashion on the patient couch;
    a first distribution structure for distribution of radiofrequency energy from the feed facility to the plurality of plug-in connectors; and
    a position generator configured to determine a relative position of the at least one movable plug-in connector with respect to the patient couch.

2. The apparatus of claim 1, wherein the first distribution structure connects at least two conduction paths of the plurality of conduction paths of the feed facility electrically to a plug-in connector of the plurality of plug-in connectors.

3. The apparatus of claim 2, wherein the first distribution structure includes a power coupler configured to combine signals of the at least two conduction paths to form one signal on one signal line.

4. The apparatus of claim 3, wherein the feed facility is a first feed facility, and
    wherein the apparatus further comprises a second feed facility for radiofrequency energy, the second feed facility having a plurality of parallel conduction paths and a second distribution structure for the distribution of radiofrequency energy from the second feed facility to the plurality of plug-in connectors.

5. The apparatus of claim 2, wherein the first distribution structure has a plurality of flexible signal lines.

6. The apparatus of claim 1, wherein the feed facility is a first feed facility, and
    wherein the apparatus further comprises a second feed facility for radiofrequency energy, the second feed facility having a plurality of parallel conduction paths and a second distribution structure for the distribution of radiofrequency energy from the second feed facility to the plurality of plug-in connectors.

7. An apparatus for use in a magnetic resonance tomography system, the apparatus comprising:
    a patient couch;
    a feed facility for radiofrequency energy, wherein the feed facility has a plurality of conduction paths for feeding radiofrequency energy;
    a plurality of plug-in connectors for local coils having a transmit coil, wherein at least one plug-in connector of the plurality of plug-in connectors is arranged in a movable fashion on the patient couch;
    a first distribution structure for distribution of radiofrequency energy from the feed facility to the plurality of plug-in connectors;
    a position generator configured to determine a relative position of the at least one movable plug-in connector with respect to the patient couch; and
    a plurality of transmitting power outputs, wherein each transmitting power output of the plurality of transmitting power outputs has an electrical connection to a conduction path of the plurality of conduction paths of the feed facility for transmission of radiofrequency energy.

8. The apparatus of claim 7, wherein the first distribution structure connects at least two conduction paths of the plurality of conduction paths of the feed facility electrically to a plug-in connector of the plurality of plug-in connectors, wherein the first distribution structure includes a power coupler configured to combine signals of the at least two conduction paths to form one signal on one signal line, and wherein the apparatus further comprises a local coil of the local coils having a transmit coil, the power coupler being provided in a housing of the local coil.

9. The apparatus of claim 7, further comprising a local coil of the local coils having a transmit coil, wherein the local coil includes a housing that is arranged in a predetermined position relative to a local coil connector.

10. The apparatus of claim 9, further comprising a controller, the controller being configured to control a transmitter pulse via the transmit coil of the local coil depending on the position of the at least one movable plug-in connector, captured by the position generator, relative to the patient couch.

11. The apparatus of claim 10, wherein a plurality of electrical connections on the feed facility are configured in releasable fashion.

12. The apparatus of claim 7, wherein a plurality of electrical connections on the feed facility are configured in releasable fashion.

13. The apparatus of claim 7, wherein the patient couch is arranged in a patient tunnel of a field magnet of the magnetic resonance tomography system, wherein the first distribution structure is arranged in the vicinity of a conducting surface such that a reaction from an alternating electromagnetic field that is emitted by a local coil of the local coils connected to a plug-in connector of the plurality of plug-in connectors is reduced.

14. The apparatus of claim 7, further comprising a plurality of power sensors and a monitoring unit, wherein the plurality of power sensors are configured to monitor a radiofrequency energy flow through a plurality of electrical connections between the plurality of transmitting power outputs and the feed facility, and the monitoring unit is configured to monitor observance of SAR limit values by values captured by the plurality of power sensors.

* * * * *